(12) United States Patent
Itu et al.

(10) Patent No.: US 10,130,266 B2
(45) Date of Patent: Nov. 20, 2018

(54) METHOD AND SYSTEM FOR PREDICTION OF POST-STENTING HEMODYNAMIC METRICS FOR TREATMENT PLANNING OF ARTERIAL STENOSIS

(71) Applicant: Siemens Healthcare GmbH, Erlangen (DE)

(72) Inventors: Lucian Mihai Itu, Brasov (RO); Puneet Sharma, Princeton Junction, NJ (US); Frank Sauer, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 587 days.

(21) Appl. No.: 14/704,233

(22) Filed: May 5, 2015

(65) Prior Publication Data

US 2015/0374243 A1  Dec. 31, 2015

Related U.S. Application Data

(60) Provisional application No. 62/018,800, filed on Jun. 30, 2014.

(51) Int. Cl.
*A61B 5/02* (2006.01)
*A61B 5/026* (2006.01)
*A61B 5/00* (2006.01)
*G06F 17/10* (2006.01)
*G16H 50/50* (2018.01)
*G06F 19/00* (2018.01)
*A61B 6/03* (2006.01)
*A61B 5/055* (2006.01)
*A61F 2/82* (2013.01)
*A61B 6/00* (2006.01)

(52) U.S. Cl.
CPC .......... *A61B 5/02007* (2013.01); *A61B 5/026* (2013.01); *A61B 5/02028* (2013.01); *A61B 5/7275* (2013.01); *G06F 17/10* (2013.01); *G06F 19/00* (2013.01); *G16H 50/50* (2018.01); *A61B 5/055* (2013.01); *A61B 6/03* (2013.01); *A61B 6/481* (2013.01); *A61B 6/504* (2013.01); *A61F 2/82* (2013.01)

(58) Field of Classification Search
None
See application file for complete search history.

(56) References Cited

U.S. PATENT DOCUMENTS

| | | | |
|---|---|---|---|
| 6,236,878 B1 | 5/2001 | Taylor et al. |
| 7,860,290 B2 | 12/2010 | Gulsun et al. |
| 7,953,266 B2 | 5/2011 | Gulsun et al. |
| 8,098,918 B2 | 1/2012 | Zheng et al. |
| 8,157,742 B2 | 4/2012 | Taylor |
| 8,200,466 B2 | 6/2012 | Spilker et al. |
| 8,249,815 B2 | 8/2012 | Taylor |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| 8,386,188 B2 | 2/2013 | Taylor et al. |
| 9,167,974 B2 † | 10/2015 | Taylor |
| 2010/0017171 A1 | 1/2010 | Spilker et al. |
| 2010/0067760 A1 | 3/2010 | Zhang et al. |
| 2011/0224542 A1 | 9/2011 | Mittal et al. |
| 2012/0022843 A1 | 1/2012 | Ionasec et al. |
| 2012/0041301 A1 | 2/2012 | Redel |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |

(Continued)

OTHER PUBLICATIONS

European Search Report for corresponding application No. 1572630. 4-1951 / 2963574 dated Dec. 22, 2015.
C.A. Taylor, et al., "Open Problems in Computational Vascular Biomechanics: Hemodynamics and Arterial Wall Mechanics," Comput Methods Appl Mech. Eng., vol. 198, pp. 3514-3523, 2009.
Chamuleau et al., "Association between coronary lesion severity and distal microvascular resistance in patients with coronary artery disease," Am J Physiol Heart Circ Physiol, vol. 285, pp. H2194-H2200, 2003.

(Continued)

*Primary Examiner* — G Steven Vanni

(57) ABSTRACT

A method and system for prediction of post-stenting hemodynamic metrics for treatment planning of arterial stenosis is disclosed. A pre-stenting patient-specific anatomical model of the coronary arteries is extracted from medical image data of a patient Blood flow is simulated in the pre-stenting patient-specific anatomical model of the coronary arteries with a modified pressure-drop model that simulates an effect of stenting on a target stenosis region used to compute a pressure drop over the target stenosis region. Parameter values for the modified pressure-drop model are set without modifying the pre-stenting patient-specific anatomical model of the coronary arteries. A predicted post-stenting hemodynamic metric for the target stenosis region, such as fractional flow reserve (FFR), is calculated based on the pressure-drop over the target stenosis region computed using the modified pressure-drop model.

50 Claims, 11 Drawing Sheets

(56) References Cited

U.S. PATENT DOCUMENTS

| | | |
|---|---|---|
| 2012/0072190 A1 | 3/2012 | Sharma et al. |
| 2012/0121151 A1 | 5/2012 | Bernhardt et al. |
| 2012/0150516 A1 | 6/2012 | Taylor et al. |
| 2012/0203530 A1 | 8/2012 | Sharma et al. |
| 2012/0243761 A1 | 9/2012 | Senzig et al. |
| 2013/0054214 A1 | 2/2013 | Taylor |
| 2013/0064438 A1 | 3/2013 | Taylor et al. |
| 2013/0090555 A1 | 4/2013 | Kassab |
| 2013/0132054 A1 | 5/2013 | Sharma |
| 2013/0246034 A1 | 9/2013 | Sharma et al. |
| 2014/0058715 A1 | 2/2014 | Sharma et al. |
| 2014/0180087 A1 | 6/2014 | Millett |
| 2015/0112182 A1 | 4/2015 | Sharma et al. |

OTHER PUBLICATIONS

De Bruyne et al., "Simultaneous Coronary Pressure and Flow Velocity Measurements in Humans," Circulation, vol. 94, pp. 1842-1849, 1996.

H. Vernon Anderson et al., "Coronary Atery Flow Velocity is Related to Lumen Area and Regional Left Ventricular Mass," Circulation, vol. 102, pp. 48-54, 2000.

† cited by third party

200

210

220

230

METHOD AND SYSTEM FOR PREDICTION OF POST-STENTING HEMODYNAMIC METRICS FOR TREATMENT PLANNING OF ARTERIAL STENOSIS

This application claims the benefit of U.S. Provisional Application No. 62/018,800, filed Jun. 30, 2014, the disclosure of which is herein incorporated by reference.

BACKGROUND OF THE INVENTION

The present invention relates to treatment planning for arterial stenosis, and more particularly, to prediction of post-stenting hemodynamic metrics for arterial stenosis.

Cardiovascular disease (CVD) is the leading cause of deaths worldwide. Among various CVDs, coronary artery disease (CAD) accounts for nearly fifty percent of those deaths. Local narrowing of a blood vessels, or stenosis, represents an important cause of cardiovascular diseases. Such stenoses typically develop gradually over time, and can develop in different parts of the arterial circulation, such as the coronary arteries, renal arteries, peripheral arteries, carotid artery, cerebral artery, etc. Such a local narrowing can also be the result of a congenital defect. One therapy widely used for treating arterial stenosis is stenting, i.e., the placement of a metal or polymer stent in the artery to open up the lumen, and hence facilitate the flow of blood. When dealing with coronary artery stenosis, the stenting therapy is referred to as percutaneous coronary intervention (PCI).

In recent years, there has been considerable focus on computational approaches for modeling the flow of blood in the human cardiovascular system. When used in conjunction with patient-specific anatomical models extracted from medical images, such computational techniques can provide important insights into the structure and function of the cardiovascular system. To predict the outcome of PCI and to plan it optimally, techniques relying on computational modeling have been proposed to perform virtual placement of the stent in an anatomical geometrical model extracted from medical images and to compute blood flow and pressure in the modified post-stenting geometry.

BRIEF SUMMARY OF THE INVENTION

The present invention provides a method and system for prediction of post-stenting hemodynamic metrics for treatment planning of arterial stenosis. Embodiments of the present invention compute post-stenting function metrics, such as flow, pressure or other derived hemodynamic metrics like fractional flow reserve (FFR), using computational modeling in conjunction with data acquired through pre-stenting medical imaging. Embodiments of the present invention do not require modification of the pre-stent geometrical model of the vessel anatomy to obtain a post-stent geometrical model. Rather, embodiments of the present invention modify a pressure-drop model to directly compute the effect of a stent on the blood flow and pressure. As a result, embodiments of the present invention, directly compute a post-stent functional model from a pre-stent anatomical model without the need for an intermediate computation of the post-stent anatomical model.

In one embodiment of the present invention, a pre-stenting patient-specific anatomical model of the coronary arteries is extracted from medical image data of a patient. Blood flow is simulated in the pre-stenting patient-specific anatomical model of the coronary arteries with a modified pressure-drop model for computing a pressure drop over a target stenosis region in the pre-stenting patient-specific anatomical model of the coronary arteries, wherein the modified pressure-drop model simulates an effect of stenting on the target stenosis region. A predicted post-stenting hemodynamic metric is calculated for the target stenosis region based on the pressure-drop over the target stenosis region computed using the modified pressure-drop model.

In another embodiment of the present invention, a pre-stenting patient-specific anatomical model of the coronary arteries is extracted from medical image data of a patient. Pre-stenting fractional flow reserve (FFR) values are calculated for a plurality of stenosis regions in the pre-stenting patient-specific anatomical model of the coronary arteries based on simulated blood flow and pressure in the pre-stenting patient-specific anatomical model of the coronary arteries. A plurality of virtual stenting strategies is determined based on the pre-stenting FFR values computed for the plurality of stenosis regions. Post-stenting FFR values are predicted for the plurality of stenosis regions resulting from each of the plurality of virtual stenting strategies, wherein each virtual stenting strategy designates one or more of the stenosis regions to be stented, and for each virtual stenting strategy, the predicted post-stenting FFR values for the plurality of stenosis regions are computed by simulating blood flow in the pre-stenting patient-specific anatomical model of the coronary arteries with a respective modified pressure-drop model used to compute a post-stenting pressure drop for each of the one or more of the stenosis regions designated to be stented in that stenting strategy.

These and other advantages of the invention will be apparent to those of ordinary skill in the art by reference to the following detailed description and the accompanying drawings.

DETAILED DESCRIPTION

Figure 1:
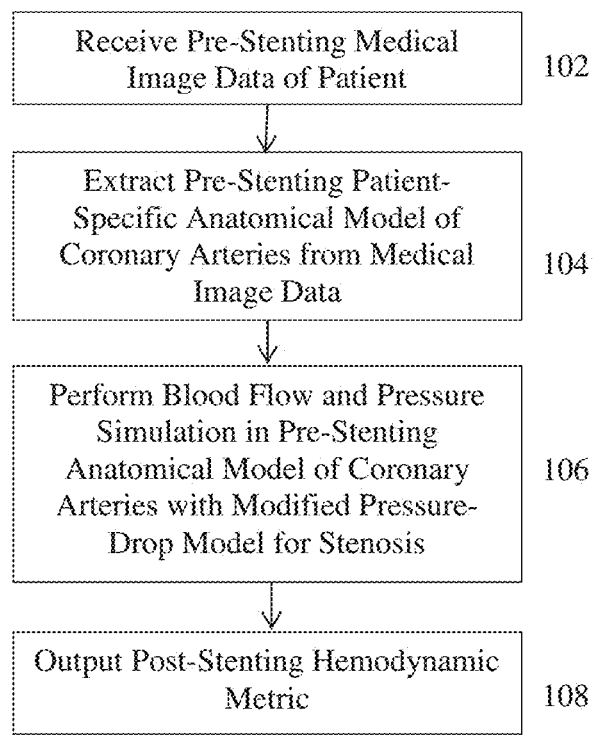
FIG. 1 illustrates a method of predicting a hemodynamic metric for one or more coronary artery stenosis of a patient according to an embodiment of the present invention.

The present invention relates to a method and system for prediction of post-stenting hemodynamic metrics for treatment planning of arterial stenosis. Embodiments of the present invention are described herein to give a visual understanding of the methods for prediction of post-stenting hemodynamic metrics for arterial stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

In order to predict the outcome of percutaneous coronary intervention (PCI) for stenting a stenosis in the coronary arteries, techniques relying on computational modeling have been proposed to perform a virtual placement of the stent in an anatomical geometrical model extracted from medical images and to compute blood flow and pressure in the modified post-stenting geometry. One common aspect in previous approaches is in the way the post-stenting anatomical model and the post-stenting functional model are generated. As used herein, the "post-stenting anatomical model" refers to geometrical model of the lumen after the stent is placed in a vessel, while the "post-stenting functional model" refers to the flow/pressure computation in the lumen after the stent has been placed in the vessel. In previous approaches, a three step procedure is used in which a 3D geometrical model of the vessel anatomy is extracted from medical images acquired pre-stenting in a first step, the pre-stent anatomical model is modified to simulate the placement of the stent in the vessel in a second step resulting in a post-stent anatomical model, and computational fluid dynamics (CFD) computations are performed in the modified post-stent anatomical model to assess the effect of the stent on the blood flow in a third step resulting in the post-stent functional model. The second step in this procedure (i.e., generating the post-stenting anatomical model) is typically achieved by modeling the stent and/or the vessel lumen as a deformable object and using techniques from computed mechanics, such as the finite element method (FEM), to solve for the deformation of the lumen due to the stent. While other techniques for modeling the stent or lumen have been proposed as well, a common theme in all of the previous approaches is the modification of the anatomical model to create a virtual post-stent geometry, which is then used for CFD simulations to compute post-stent flow and pressure related metrics. It should be noted that the generation of the post-stenting anatomical model is a complex step, which requires many assumptions, such as the material property of the vessel wall, accurate geometry and material properties of the stent, the balloon force (or the pre-stress in the case of self-expanding stents), etc. Furthermore, the pre-stenting anatomical model must be modified to create a different post-stenting anatomical model to model PCI stenting for each stenosis or combination of stenoses.

Embodiments of the present invention are advantageous in that the post-stenting functional model is directly obtained using the pre-stenting anatomical model without generating the post-stent anatomical model. Embodiments of the present invention can utilize a hybrid, or multi-scale computational model for computation of blood flow and pressure in the coronary arteries, which uses reduced-order pressure-drop models to model the loss of pressure across a stenosis or any other narrowing in a vessel. The pressure-drop models compute the effective pressure drop that occurs due to the narrowing of the vessel (e.g., stenosis, calcification, thrombus, bifurcations, etc.) without performing an explicit flow computation in that region of the vessel. Embodiments of the present invention compute post-stenting fractional flow reserve (FFR) or other hemodynamic metrics for a coronary artery stenosis using computational modeling in conjunction with pre-stent medical image data of a patient. Embodiments of the present invention do not require obtaining modification of the pre-stenting geometrical model of the vessel anatomy to first obtain a post-stenting geometrical model prior to computing the post-stenting hemodynamic metrics. Rather, embodiments of the present invention compute the effect of a stent on the blood flow and pressure by directly modifying the pressure-drop model for a particular stenosis. As a result, embodiments of the present invention directly compute a post-stenting functional model without the need for an intermediate computation of a post-stenting anatomical model. Embodiments of the present invention are described herein for predicting post-stenting hemodynamic metrics for coronary artery stenosis for PCI treatment planning. However, it is to be understood that the methods described herein can be similarly applied to predict post-stenting hemodynamic metrics to other types of arteries as well, such as the renal arteries, peripheral arteries, carotid artery, cerebral artery, etc. The methods described herein can also be applied to other parts of the circulatory system, such as for venous circulation or pulmonary circulation. Embodiments of the present invention can also be applied to treatment planning for airways.

FIG. 1 illustrates a method of predicting a hemodynamic metric for one or more coronary artery stenosis of a patient according to an embodiment of the present invention. Referring to FIG. 1, at step 102, pre-stenting medical image data of a patient is received. The pre-stenting medical image data is acquired prior to performing stenting, such as PCI for a coronary artery stenosis. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on a patient-specific anatomical model that is extracted from the image data (step 104). Alternatively, the stenoses may be automatically detected in the image data using an algorithm for automatic detection of coronary artery stenosis, such as the method for automatic detection of coronary artery stenosis described in United States Published Patent Application No. 2011/0224542, which is incorporated herein by reference. In addition to the medical image data, other non-invasive clinical measurements, such as the patient's heart rate and systolic and diastolic blood pressure may also be acquired. These non-invasive clinical measurements can be used to establish boundary conditions for CFD computations.

At step 104, a pre-stenting patient-specific anatomical model of the coronary arteries is extracted from the pre-stenting medical image data. The patient-specific anatomical model may be a patient-specific anatomical model of any portion of the full coronary artery tree of the patient. In order to generate the patient-specific anatomical model of the coronary artery tree, the coronary arteries can be segmented in the 3D medical image data using an automated coronary artery centerline extraction algorithm. For example, the coronary arteries can be segmented in a CT volume using the method described United States Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. No. 7,860,290 and U.S. Pat. No. 7,953,266, both of which are incorporated herein by reference. In addition to the coronaries, the patient-specific anatomical model can include the aortic root together with the proximal part of the aorta. A detailed 3D model of each stenosis can also be extracted using similar algorithms, which includes the quantification of the proximal vessel diameter and area, distal vessel diameter and area, minimal lumen diameter and area, and length of stenosis.

Figure 2:
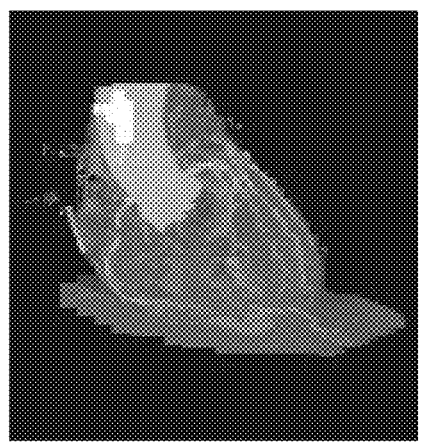
FIG. 2 illustrates exemplary results for generating a pre-stenting patient-specific anatomical model of the coronary vessel tree.
Figure 2:
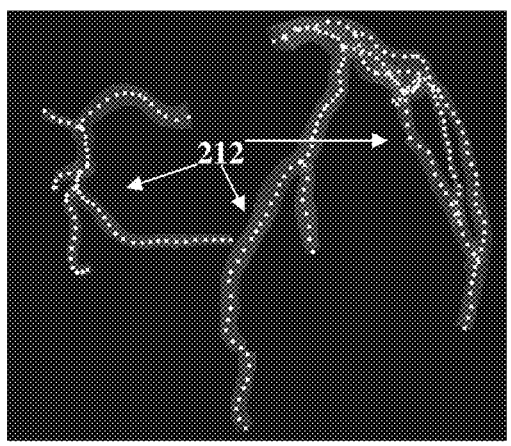
Figure 2:
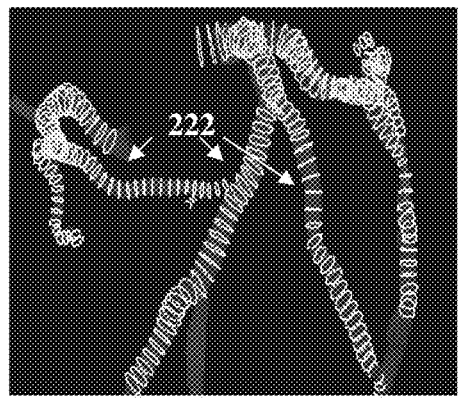
Figure 2:
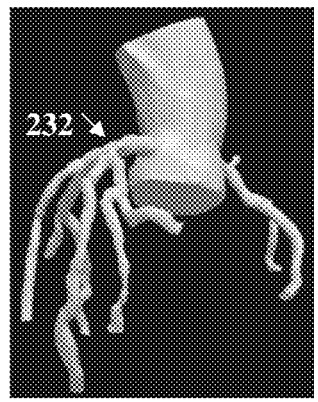

FIG. 2 illustrates exemplary results for generating a pre-stenting patient-specific anatomical model of the coronary vessel tree. Image 200 of FIG. 2 shows coronary CTA data. Image 210 shows a centerline tree 212 extracted from the CTA data. Image 220 shows cross-section contours 222 extracted at each point of the centerline tree 212. Image 230 shows a 2D surface mesh 232 of the coronary arteries, the aortic root, and the proximal part of the aorta. It is to be understood that the anatomical model of the coronary tree of the patient can be output and displayed, for example on a display screen of the computer system.

The above described anatomical modeling tasks can be performed automatically or can be user-driven, thereby allowing the user (clinician) to interactively make changes to the anatomical models to analyze the effects of such changes on the subsequent computation of FFR. In addition to the coronary vessel tree, the myocardium may also be segmented (either automatically or manually) in the medical image data to determine an estimate of the left ventricular mass, which in a possible implementation, may be used to estimate the absolute resting flow for the patient which is used to calculate boundary conditions for a computational blood flow and pressure simulation. Alternatively, the resting flow could also be computed based on the total volume of the segmented coronary tree, or from the outlet radius of the different coronary vessels. In an exemplary embodiment, a patient-specific anatomical model of the heart that is automatically generated from the image data may be used for this purpose. The anatomical heart model is a multi-component model having multiple cardiac components, including the four chambers (left ventricle, left atrium, right ventricle, and right atrium). The anatomical heart model may also include components such as the heart valves (aortic valve, mitral valve, tricuspid valve, and pulmonary valve) and the aorta. Such a comprehensive model of the heart is used to capture a large variety of morphological, functional, and pathological variations. A modular and hierarchical approach can be used to reduce anatomical complexity and facilitate an effective and flexible estimation of individual anatomies. The 4D anatomical heart model can be generated by generating individual models of each heart component, for example using marginal space learning (MSL), and then integrating the heart component models by establishing mesh point correspondence. Additional details regarding generation of such a 4D patient-specific heart model are described in United States Published Patent Application No. 2012/0022843, which is incorporated herein by reference in its entirety.

At step 106, blood flow and pressure are simulated in the pre-stenting anatomical model of the coronary arteries using a modified pressure-drop model for a coronary artery stenosis. In particular, the blood flow is simulated in the pre-stenting anatomical model of the coronary arteries and a post stenting pressure-drop for the stenosis is calculated based on the simulated blood flow using the modified pressure-drop model. The blood flow and pressure can be simulated in the pre-stenting anatomical model using CFD computations or any other standard numerical technique, such as finite-element method, finite-difference method, finite volume method, boundary element method, embedded boundary method, immersed boundary method lattice Boltzmann method, etc. According to an advantageous embodiment of the present invention, a multi-scale computational model of coronary circulation can be used to compute the blood flow and pressure in the pre-stenting anatomical model of the coronary arteries over a series of time steps. For example, the simulation may be performed for a plurality of time steps corresponding to a full cardiac cycle or multiple cardiac cycles. The computational model of the coronary circulation models the loss of pressure across stenoses or other narrowings in the coronary arteries (e.g., calcification, thrombus, bifurcation, etc.) using pressure-drop models. It is to be understood that throughout this disclosure, the term stenosis is used to generally refer to any type of narrowing in a vessel. The pressure drop model for a particular stenosis computes the pressure drop over the stenosis due to the narrowing of the vessel without performing an explicit flow computation in that region of the vessel.

Figure 3:
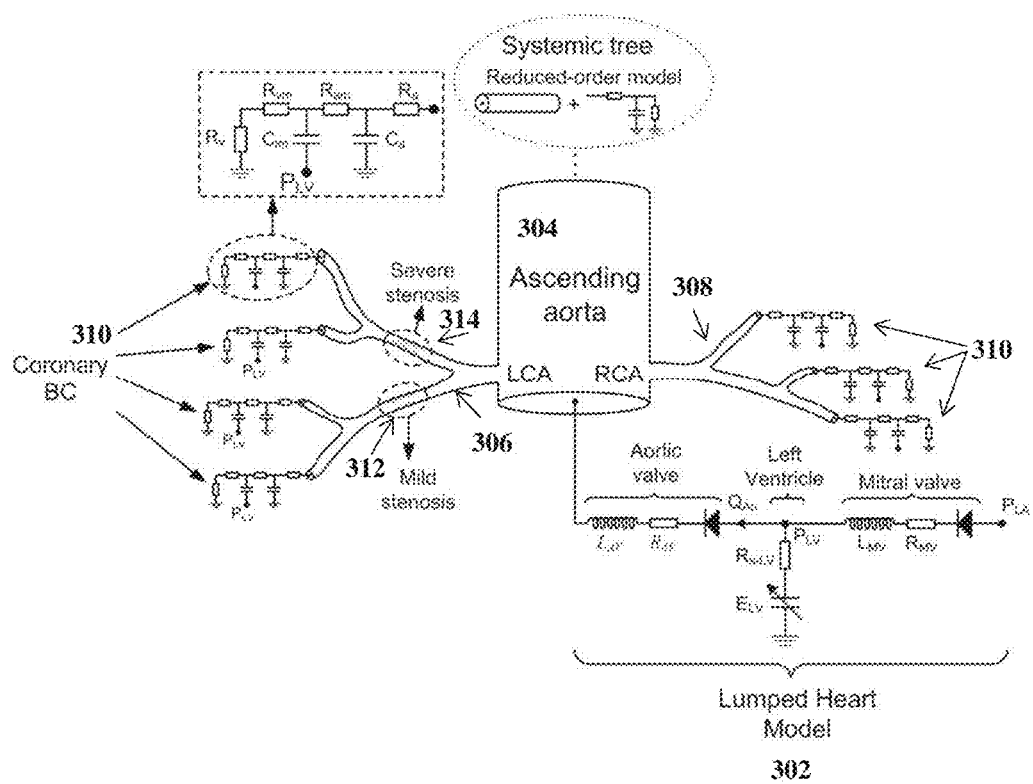
FIG. 3 illustrates an exemplary multi-scale computational model of coronary circulation according to an embodiment of the present invention.

FIG. 3 illustrates an exemplary multi-scale computational model of coronary circulation according to an embodiment of the present invention. As shown in FIG. 3, a heart model 302 is coupled at the root of the aorta. The heart model 302 may be implemented as a lumped model parameterized through patient-specific data as shown in FIG. 3, or may be implemented as a full 3D heart model. Large arteries, such as the aorta 304 together with the large arteries supplied by the aorta (e.g., subclavian, brachiocephalic, common carotid, etc.), the left coronary artery (LCA) 306, and the right coronary artery (RCA) 308 can be represented as 1D blood flow models or full 3D models. Furthermore, semi-analytical circulatory models can be used either separately for certain arterial segments, or embedded within the 1D or 3D models. The vessel walls can be modeled as a purely elastic or visco-elastic material. The wall properties may be determined through an empirical relationship fit to measured data or based on patient-specific estimations of wall compliance. In the model of coronary arterial circulation of FIG. 3, all microvascular beds are simulated through lumped parameter models 310 which account for the resistance applied to the blood flow and for the compliance of the distal vessels. The coronary vascular bed is modeled through such lumped parameter models 310, which are adapted to the coronary circulation in the sense that they take into account the effects of the myocardial contraction on the flow waveform. Stenosis segments 312 and 314 (i.e., regions in the vessels where a stenosis or a narrowing is detected) are shown in the model of coronary arterial circulation. The stenosis segments 312 and 314 cannot be simulated using the 1D blood flow models since there is a high variation in cross-sectional area and the shape of the stenosis influences the blood flow behavior and especially the trans-stenotic pressure drop which plays a major role in the assessment of the functional importance of such a stenosis. According to an advantageous embodiment of the present invention, a reduced-order (as compared to a full 3D model) pressure-drop model can be used for each stenosis segment 312 and 314. Additional details regarding the multi-scale computational model of coronary circulation, as well as calculating rest-state and hyperemia-state boundary conditions for the blood flow and pressure computations, are described in United States Patent Publication No. 2013/0132054, entitled "Method and System for Multi-Scale Anatomical and Functional Modeling of Coronary Circulation," United States Patent Publication No. 2013/0246034, entitled "Method and System for Non-Invasive Functional Assessment of Coronary Artery Stenosis," and United States Patent Publication No. 2014/00058715, entitled "Method and System for Non-Invasive Functional Assessment of Coronary Artery Stenosis," and U.S. application Ser. No. 14/689,083, entitled "Method and System for Non-Invasive Computation of Hemodynamic Indices for Coronary Artery Stenosis," which are incorporated herein in their entirety by reference.

As described above, a pressure-drop model is used to compute the pressure-drop across each stenosis region (e.g., 312 and 314 of FIG. 3) in the pre-stenting anatomical model of the coronary arteries without performing an explicit flow computation in the stenosis region. Various pressure-drop models can be used. For example, the pressure-drop model for a stenosis may be a fully analytical model or may be a model that includes a combination of analytical and empirical terms. A pressure-drop model that includes a combination of analytical and empirical terms is referred to herein as a "semi-empirical pressure-drop model". Other pressure-drop models may be used as well, such as a machine-learning based pressure-drop model that is trained using a machine-learning algorithm to map anatomical and flow features derived from a stenosis to a pressure-drop associated with the stenosis. According to an advantageous embodiment, in order to predict the effect of stenting a coronary artery stenosis, the pressure-drop model for the stenosis is directly modified and the blood flow and pressure simulation in the pre-stenting anatomical model of the coronary arteries is performed with the modified pressure drop model. As used herein, "directly modifying" the pressure-drop model for the coronary artery stenosis refers to modifying parameters in the pressure-drop model without modifying the underlying pre-stent patient-specific anatomical model of the coronary arteries. The pressure-drop model for the stenosis can be modified to represent a fully successful treatment or a partially successful treatment. The goal of the modification of the pressure-drop model is to virtually simulate the effect of the enlargement of the vessel due to stenting without explicitly modifying the actual patient-specific geometry. Examples of modifying a pressure-drop model to represent partially successful and fully successful treatments are described below for a fully analytical pressure-drop model and a semi-empirical pressure drop model. It is to be understood that the present invention is not limited to these specific examples and may be similarly applied to other pressure-drop models as well.

Fully Analytical Pressure-Drop Model

In an exemplary implementation, a fully analytical pressure-drop model for a stenosis can be given by the following equation:

$$\Delta P = \frac{\rho Q^2}{2}\left(\frac{1}{CSA_{out}^2} - \frac{1}{CSA_{in}^2}\right) + \frac{\rho Q^2}{2}\frac{96}{5}\int_1^\alpha \frac{1+4\alpha+9\alpha^2+4\alpha^3}{\alpha(3+\alpha)(3+2\alpha+\alpha^2)}d\alpha + \int_0^{L_{vessel}-L_{sten}} \frac{8\mu\pi}{CSA^2}Q dx + \frac{\rho Q^2}{2}\left\{\left(\frac{1}{CSA_{sten}} - \frac{1}{CSA_{out}}\right)^2 + \left[2\left(\frac{1}{CSA_{sten}} - \frac{1}{CSA_{out}}\right)\left(\frac{1}{CSA_{sten}} - \frac{1}{3}\frac{1}{CSA_{out}}\right) - \left(\frac{1}{CSA_{sten}} - \frac{1}{CSA_{out}}\right)^2\right](1-\alpha)^2\right\}$$

(1)

Figure 4:
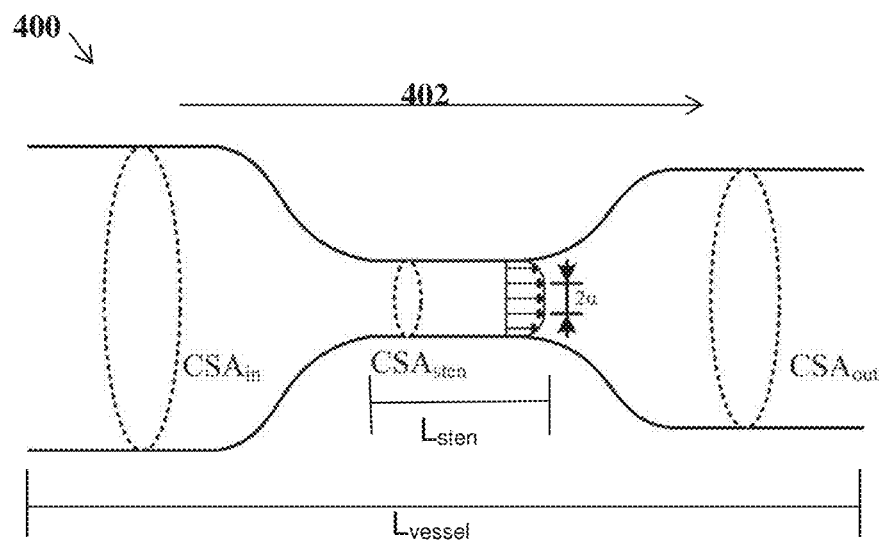
FIG. 4 illustrates parameters of the pressure drop model for an exemplary stenosis segment.

In Equation (1), $\Delta P$ denotes the pressure drop over the stenosis region of the vessel, Q denotes flow rate, $\rho$ denotes the density of blood, $\mu$ denotes viscosity, and x denotes a position along the centerline of the vessel in the stenosis region. FIG. 4 illustrates parameters of the pressure drop model for an exemplary stenosis segment. As shown in FIG. 4, arrow 402 represents a direction of blood flow through a stenosed segment 400 of a coronary artery. The proximal or input side of the stenosed segment 400 is referred to as the "top" and the distal or output side of the stenoses segment 400 is referred to as the "bottom". $CSA_{in}$ is the cross-sectional area at the top of the stenosed segment. $CSA_{out}$ is the cross-sectional area at the bottom of the stenosed segment. $CSA_{sten}$ is the minimum cross-sectional area along the stenosis. In Equation (1), CSA refers to the cross section area at a given point x in the stenosed segment. $\alpha$ denotes the dimensionless radius of the inviscid core, in which the flow velocity is uniform. $\alpha$=radius at the inlet of the stenosis, 0<$\alpha$<radius from the inlet to the region with fully developed flow, and $\alpha$=0 in the region with fully developed flow. $L_{sten}$ refers to the length of the stenosis region in which the radius is minimum and constant, and $L_{vessel}$ refers to the entire length of the stenosed segment for which the pressure drop is calculated. The fully analytical pressure-drop model of Equation (1) includes three pressure drop calculations. The first term of Equation (1) calculates the convection pressure drop, the second and third terms calculate the viscous pressure drop, and the fourth term calculates the expansion pressure drop.

According to an advantageous embodiment of the present invention two modified post-treatment (post-stenting) pressure-drop models can be calculated by modifying the fully analytical pressure drop model of Equation (1), corresponding to partially successful treatment of the stenosis region and fully successful treatment of the stenosis region.

In order to simulate the effect of partially successful treatment, the virtual post-stenting pressure drop model can be calculated by generating assumed values for the following two parameters: the cross-sectional area in the distal (bottom) part of the stenosis segment ($CSA_{out\_post}$) and the minimum cross-sectional area value along the stenosis ($CSA_{sten\_post}$). $CSA_{out\_post}$ can be set to be either equal to the pre-treatment value ($CSA_{out}$) or greater. For example, if the cross-section area in the proximal part of the stenosed segment ($CSA_{in}$) is larger than the pre-treatment value for $CSA_{out}$, $CSA_{out\_post}$ can be set to a value greater than or equal to $CSA_{out}$ and less than or equal to $CSA_{in}$. $CSA_{sten\_post}$ is set to a value that is greater than the pre-treatment value $CSA_{sten}$, but less than $CSA_{in}$ and $CSA_{out\_post}$, thus representing a case in which the enlargement of the stenosis region is only partially successful. For example, $CSA_{sten\_post}$ can be set to be a predetermined percentage of $CSA_{in}$ or $CSA_{out\_post}$, and the percentage can be tuned to predict the effect of the treatment at various levels of partial success. In a possible embodiment, $CSA_{sten\_post}$ can be set to percentage of $CSA_{in}$ or $CSA_{out\_post}$ that is automatically determined based on calcifications in the medical image data. This embodiment is described in greater detail below. The following post-stenting pressure drop model for partially successful treatment can then be used:

$$\Delta P = \frac{\rho Q^2}{2}\left(\frac{1}{CSA_{out-post}^2} - \frac{1}{CSA_{in}^2}\right) + \int_0^{L_{vessel}} \frac{8\mu\pi}{CSA^2} Q dx + \frac{\rho Q^2}{2} \quad (2)$$

$$\left\{\left(\frac{1}{CSA_{sten-post}} - \frac{1}{CSA_{out-post}}\right)^2 + \left[2\left(\frac{1}{CSA_{sten-post}} - \frac{1}{CSA_{out-post}}\right)\right. \right.$$

$$\left(\frac{1}{CSA_{sten-post}} - \frac{1}{3}\frac{1}{CSA_{out-post}}\right) -$$

$$\left.\left.\left(\frac{1}{CSA_{sten-post}} - \frac{1}{CSA_{out-post}}\right)^2\right](1-\alpha)^2\right\}$$

In the post-stenting pressure drop model of Equation (2), the convection pressure drop term (first term) is computed based on the assumed value of the cross-sectional area in the distal part of the stenosed segment $CSA_{out\_post}$. The first of the two viscous pressure drop terms in Equation (1) is removed and the second viscous pressure drop term (second term in Equation (2)) is used to compute the viscous pressure drop along the entire stenosed segment. The expansion pressure-drop term (third term of Equation (2)) is computed based on the new assumed values of the minimum and distal cross-sectional areas $CSA_{sten\_post}$ and $CSA_{out\_post}$, respectively.

For the fully successful post-stenting pressure-drop model, the effect of the treatment can be simulated by generating a single assumed value for the cross-sectional area in the distal part of the stenosed segment $CSA_{out\_post}$. Once again, the value for $CSA_{out\_post}$ can be selected to be either equal to $CSA_{out}$ or greater. For example, if $CSA_{in}$ is larger than $CSA_{out}$, then $CSA_{out\_post}$ can be set to a value greater than or equal to $CSA_{out}$ and less than or equal to $CSA_{in}$. In a possible implementation, $CSA_{out\_post}$ can be set equal to $CSA_{in}$. This implementation assumes that the cross-section area is uniform and fully expanded along the entire stenosed segment such that $CSA_{in}=CSA_{sten\_post}=CSA_{out\_post}$. Once the assumed value is set for $CSA_{out\_post}$, the following post-treatment pressure drop model for fully successful treatment can be used:

$$\Delta P = \quad (3)$$

$$\frac{\rho Q^2}{2}\left(\frac{1}{CSA_{out-post}^2} - \frac{1}{CSA_{in}^2}\right) + \frac{8\mu\pi}{((CSA_{in} + CSA_{out\_post})/2)^2} Q \cdot L_{vessel}$$

In the post-stenting pressure drop model of Equation (3), the convection pressure term (first term) is computed based on the assumed value of the cross-section area in the distal part of the stenosed segment $CSA_{out\_post}$, while the viscous pressure drop is computed based on the average value of $CSA_{in}$ and $CSA_{out\_post}$. In an alternative implementation, an interpolation (e.g., linear, quadratic, etc.) between the values of $CSA_{in}$ and $CSA_{out\_post}$ can be used to compute the viscous pressure drop instead of the average value of $CSA_{in}$ and $CSA_{out\_post}$. The expansion pressure drop term is removed completely since the turbulent flow regime is inexistent in this case.

Semi-Empirical Pressure-Drop Model

In this exemplary implementation, the semi-empirical pressure-drop model for a coronary artery stenosis can be derived by starting with a model that predicts the pressure drop based on empirical data and augmenting the empirical model with an analytical convection pressure-drop term. For example, an empirical model that computes the pressure-drop for a stenosis based on viscous, turbulent, and inertance coefficients can be expressed as:

$$\Delta P = \frac{\mu K_v}{2\pi r_0^3}q + \frac{\rho K_t}{2CSA_{out}^2}\left(\frac{CSA_{out}}{CSA_{sten}} - 1\right)^2|q|q + \frac{\rho K_u L_s}{CSA_{out}}\frac{\partial q}{\partial t}, \quad (4)$$

where $\Delta P$ denotes the pressure drop over the stenosed segment of the vessel, q denotes flow rate, $\rho$ denotes the density of blood, $\mu$ denotes the blood viscosity, $L_s$ denotes the stenosis length, $r_0$ denotes the vessel radius in a normal (non-stenosis) portion of the vessel, and $K_v$, $K_t$, and $K_u$ are the viscous, turbulent, and inertance coefficients, respectively, which are empirically determined. Quantities indexed with 0 refer to the normal vessel, while quantities indexed with s refer to the stenosis. Before introducing modifications for the post-treatment model, the empirical pressure drop model of Equation (4) can be augmented with a convection pressure-drop term, resulting in the following semi-empirical pressure drop model:

$$\Delta P = \frac{\rho q^2}{2}\left(\frac{1}{CSA_{out}^2} - \frac{1}{CSA_{in}^2}\right) + \quad (5)$$

$$\frac{\mu K_v}{2\pi r_0^3}q + \frac{\rho K_t}{2CSA_{out}^2}\left(\frac{CSA_{out}}{CSA_{sten}} - 1\right)^2|q|q + \frac{\rho K_u L_s}{CSA_{out}}\frac{\partial q}{\partial t}.$$

Again, two post-stenting pressure-drop models can be calculated by modifying the semi-empirical pressure drop model of Equation (5), corresponding to a partially successful treatment and a fully successful treatment. The modified post-stenting pressure-drop model for the partially successful treatment of the stenosis region can be expressed as:

$$\Delta P = \frac{\rho q^2}{2}\left(\frac{1}{CSA_{out-post}^2} - \frac{1}{CSA_{in}^2}\right) + \frac{\mu K_v}{2\pi r_0^3}q + \quad (6)$$

$$\frac{\rho K_t}{2CSA_{out-post}^2}\left(\frac{CSA_{out-post}}{CSA_{sten-post}} - 1\right)^2|q|q + \frac{\rho K_u L_s}{CSA_{out}}\frac{\partial q}{\partial t}.$$

In Equation (6), the first three terms are adapted by setting assumed values for $CSA_{out\_post}$ and $CSA_{sten\_post}$ as described above, and by adapting $K_v$ correspondingly. In particular, $K_v$ can be determined as a function of the cross-sectional area along the centerline of the stenosis. In an exemplary implementation, the cross-sectional area is interpolated between $CSA_{in}$, $CSA_{sten\_post}$, and $CSA_{out\_post}$. The modified post-stenting pressure-drop model for the fully successful treatment of the stenosis region can be expressed as:

$$\Delta P = \frac{\rho q^2}{2}\left(\frac{1}{CSA_{out-post}^2} - \frac{1}{CSA_{in}^2}\right) + \frac{\mu K_v}{2\pi r_0^3}q + \frac{\rho K_u L_s}{CSA_{out}}\frac{\partial q}{\partial t}. \quad (7)$$

In Equation (7), the first two terms are adapted by setting the assumed value for $CSA_{out\_post}$, as described above, and by adapting $K_v$ correspondingly, while the third term from Equation (5) is dropped completely due to the absence of the turbulent flow regime. The inertance term (the fourth term in Equation (5)) remains the same in both Equations (6) and (7) since this term only introduces a phase shift between pressure and flow and does not contribute to the total pressure drop.

Figure 5:
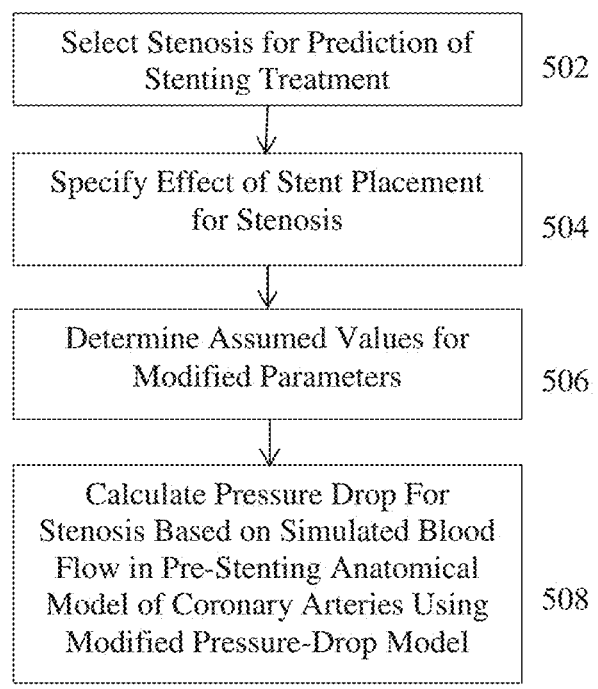
FIG. 5 illustrates a method for modifying a pressure drop model and calculating a pressure-drop over a coronary artery stenosis according to an embodiment of the present invention.

FIG. 5 illustrates a method for modifying a pressure drop model and calculating a pressure-drop over a coronary artery stenosis according to an embodiment of the present invention. The method of FIG. 5 may be used in the implementation of step 106 of FIG. 1. The method of FIG. 5 can be performed interactively based on user input entered by a user using a user input device, such as a mouse or touch screen, automatically without user input, or some combination thereof. Referring to FIG. 5, at step 502, a stenosis is selected for virtual stenting treatment prediction (e.g., virtual PCI). As described above, stenosis regions in the coronary artery tree can be manually identified by a user or automatically detected. In step 502, a stenosis region or multiple stenosis regions in the coronary artery tree are selected for stenting treatment prediction. In one possible implementation, the stenosis region (or multiple stenosis regions) can be selected interactively by a user. For example, the patient-specific anatomical model of the coronary artery tree and/or the medical image data of the patient can be displayed on a display device of a computer and a user can select on stenosis region or multiple stenosis regions for which to predict the effect of the stenting treatment. The user input selecting the stenosis region may be received in response to a prompt displayed on the display device requesting that the user select a stenosis region. In another possible implementation, the stenosis region can be automatically selected by a computer/processor without user input. For example, the computer can automatically perform the treatment prediction for multiple possible treatment scenarios, where each treatment scenario corresponds to stenting a stenosis region or multiple stenosis regions in the coronary artery tree of the patient.

At step 504, an effect of the stent placement is specified for the selected stenosis. In particular, it is determined if the virtual stenting is partially successful, corresponding to partial enlargement of the stenosis, or fully successful, corresponding to complete enlargement of the stenosis. The selection of partially successful treatment or fully successful treatment determines which modified pressure-drop model to use. In one possible implementation, the selection of partially successful treatment or fully successful treatment can be performed interactively by a user. For example, in response to a user selecting a stenosis for virtual treatment prediction, a prompt can be displayed on the displayed device providing the user a choice between the partially successful treatment and the fully successful treatment. If the user selects partially successful treatment, the user may be given a further prompt to select a percentage corresponding to how successful the treatment is (i.e., percentage of enlargement of vessel geometry in the stenosis). The user may also be given the option to select a type of the pressure-drop model, such as the fully analytical model or the semi-empirical model, or the type of pressure-drop model can be preset and not selectable by the user. It is important to note that the determination of partially successful treatment or fully successful treatment is not based on modification of the anatomical model of the coronary arteries to estimate the actual enlargement of the geometry due to stent placement.

In another possible implementation, the determination of partially successful treatment or fully successful treatment can be performed automatically based on the medical image data of the patient. In this implementation, features from the medical image may be extracted to automatically determine the probability that the PCI procedure would result in a partial or a complete enlargement of the stenosed region. For example, the amount of calcification may be quantified for each stenosis by analyzing the intensity values of the image voxels in a region of interest (in this case, a region around the stenosis). A stenosis with a high amount of calcification is more likely to result in a partial opening of the stent as compared to a stenosis with no calcification. Other features, such as tortuosity of the vessel or the radius of the vessel, can also be quantified similarly to determine a composite index which relies on more than one feature from the medical image data. In addition to automatically selecting a partially successful treatment or fully successful treatment for a stenosis, the features can be used to automatically select a percentage of enlargement to use for the partially successful treatment.

At step 506, assumed values for the modified parameters of the modified pressure-drop model are set. The number and type of the parameters depends on the effect of the stent (i.e., partially successful treatment or fully successful treatment) specified in step 506. The assumed values for the modified parameters for the partially successful treatment pressure-drop model or for the fully successful treatment pressure-drop model can be set as described above. At step 508, the pressure drop for the selected stenosis is determined based on the simulated blood flow in the pre-stenting anatomical model of the coronary arteries using the modified post-stenting pressure-drop model with the assumed values for the modified parameters determined in step 506.

Returning to FIG. 1, at step 108, a hemodynamic metric is calculated for the coronary artery stenosis. During the blood flow and pressure simulation of step 106, the post-stenting pressure-drop is computed for the stenosis for each of a series of time steps. According to an advantageous embodiment of the present invention, a post-stenting fractional flow reserve (FFR) is calculated for the stenosis based on the post-stenting pressure drop computed for the stenosis. FFR is defined as the ratio of the maximal blood flow in the stenotic vessel to the maximal blood flow in a normal vessel, and is used to characterize the severity of the stenosis. FFR can be approximated for a stenosis by calculating the ratio of the time-averaged pressure distal to the stenosis (Pd) with respect to the average pressure in the aorta (Pa) at the hyperemic state. Accordingly, in an advantageous embodiment, the blow flow simulation in step 106 simulates hyperemic blood flow, and the computed post-stenting pressure drop for the stenosis can be averaged over a heart cycle and subsequently used to determine the post-stenting FFR value for the stenosis. In particular, FFR can be computed as $(Pa-\Delta P)/Pa$, where Pa is the aortic pressure. The aortic pressure may be assumed at a population average value or may be determined as a function of the non-invasively acquired systolic and diastolic pressures, and the heart rate. Other hemodynamic metrics can be calculated for the stenosis as well. For example, hemodynamic metrics, such as instantaneous wave-free ratio (iFR) and rest Pd/Pa, can be calculated based on the post-stenting pressure-drop for a stenosis resulting from rest-state blood flow simulations. The post-stenting FFR value and/or other post-stenting hemodynamic metrics can be output by displaying the values on a display device. In a possible implementation, one or more computed post-stenting FFR values (or other hemodynamic metrics) can be visualized on a medical image of the patient that is displayed on a display device.

Figure 6:
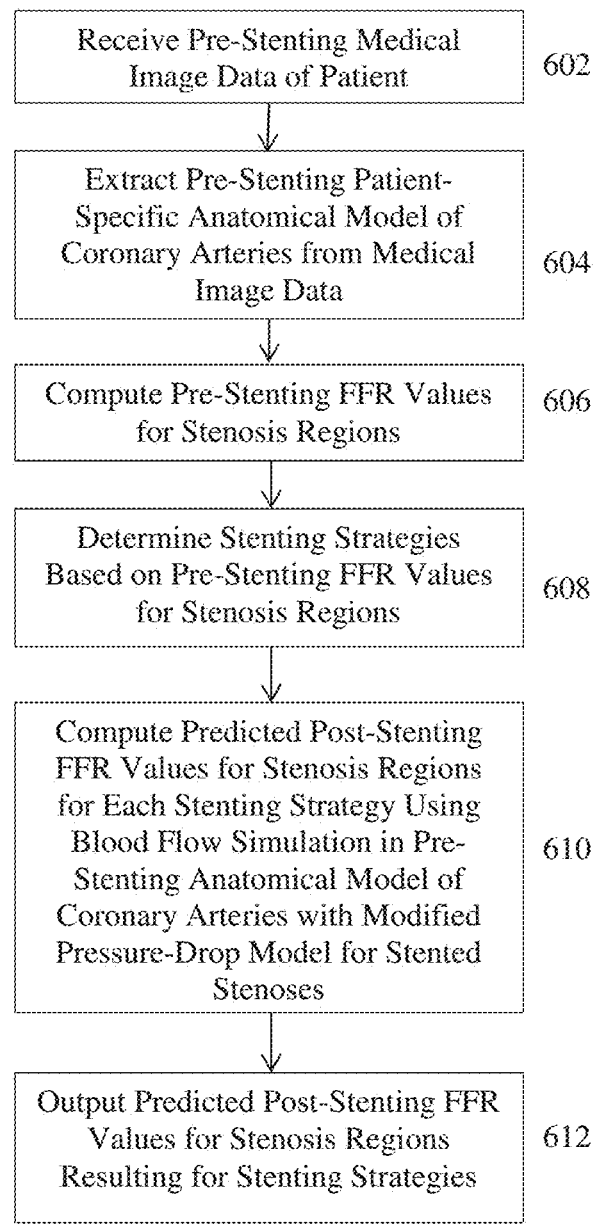
FIG. 6 illustrates a method of stent treatment planning according to an embodiment of the present invention.

FIG. 6 illustrates a method of stent treatment planning according to an embodiment of the present invention. The method of FIG. 6 is described herein using the example of planning PCI treatment for coronary artery stenoses of a patient, but the present invention is not limited thereto and can be similarly applied to other stenting treatments in other types of arteries. The method of FIG. 6 can be used to evaluate different stenting strategies for treating coronary artery stenoses to determine which stenting strategies are effective and/or select a best stenting strategy. The method of FIG. 6 can be implemented as fully automated method for stent treatment planning. Referring to FIG. 6, at step 602, medical image data of a patient is received. At step 604, a pre-stenting patient-specific anatomical model of the coronary arteries is extracted from the medical image data. Steps 602 and 604 are identical to steps 102 and 104 of FIG. 1. As described above, stenosis regions can be automatically detected or manually identified in the medical image data or in the pre-stenting patient-specific anatomical model of the coronary arteries.

At step 606, pre-stenting FFR values are computed for each of the stenosis regions in the pre-stenting patient-specific anatomical model of the coronary arteries. The pre-stenting FFR values can be computed by simulating blood flow and pressure at a hyperemic state in the pre-stenting patient-specific anatomical model of the coronary arteries. For example, the computational model of coronary circulation can be used to perform the blood flow and pressure computations.

At step 608, a plurality of stenting strategies are determined based on the pre-stenting FFR values computed for the stenosis regions in the pre-stenting patient-specific anatomical model of the coronary arteries. In particular, stenosis regions having a pre-stenting FFR value less than a predetermined threshold (e.g., <0.8) are identified as target stenosis regions for stenting. In addition, for each stenosis region having a pre-stenting FFR value less than the threshold, all preceding stenosis regions (i.e., in the proximal direction) in a blood flow path in the coronary artery tree are also identified as target stenosis regions for stenting. A plurality of stenting strategies can be generated for each set of target stenosis regions in a particular blood flow path in the coronary artery tree, where each stenting strategy corresponds to stenting a subset of the target stenosis regions. The stenting strategies include a stenting strategies corresponding to stenting each individual target stenosis region and stenting strategies corresponding to stenting each possible combination of multiple target stenosis regions, up to a stenting strategy corresponding to stenting all of the target stenosis regions.

Figure 7:
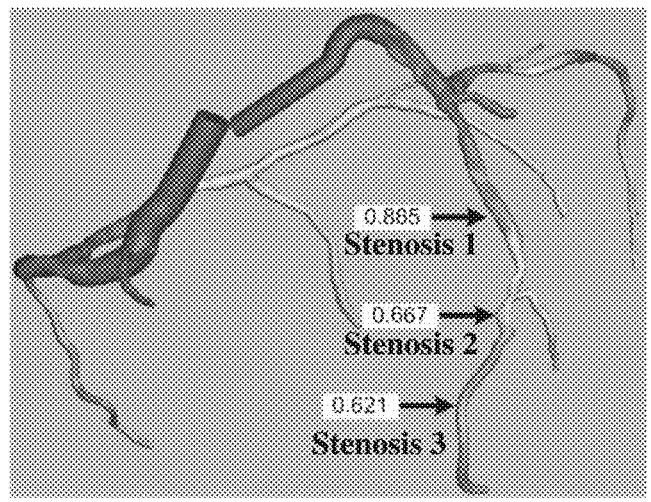
FIG. 7 illustrates exemplary pre-stenting FFR computation results for three stenosis regions in a coronary artery tree.

FIG. 7 illustrates exemplary pre-stenting FFR computation results for three stenosis regions in a coronary artery tree. As shown in FIG. 7, the left anterior descending (LAD) artery has three serial stenoses (stenosis 1, stenosis 2, and stenosis 3), each of which may or may not be hemodynamically significant. Stenosis 1 has a pre-stenting FFR value of 0.885, stenosis 2 has a pre-stenting FFR value of 0.667, and stenosis 3 has a pre-stenting FFR value of 0.621. Since the most distal stenosis (stenosis 3) has an FFR value smaller 0.8, it is clear that PCI has to be performed, and all three stenoses are identified as target stenoses for stenting. The goal of the virtual planning method of FIG. 6 is to determine the stenoses for which PCI should be performed. In FIG. 7, the pre-stenting FFR values indicate that stenosis 2 is the most significant since it leads to the largest drop in FFR value. However, it is unclear if stenting stenosis 2 suffices for raising the distal FFR value (of stenosis 3) above 0.8

Returning to FIG. 6, at step 610, for each of the plurality of stenting strategies, predicted post-stenting FFR values are computed for the each of the target stenosis regions by simulating blood flow in the pre-stenting patient-specific anatomical model of the coronary arteries using a modified pressure-drop model for the target stenosis region that is stented in the current stenting strategy. In particular, the method of FIG. 1 can be implemented to predict the effect of the stenting of each target stenosis region to be stented in a current stenting strategy by calculating predicted post-stenting pressure drop for each target stenosis region to be stented based on the simulated blood flow in the pre-stenting patient-specific anatomical model of the coronary arteries using a respective modified post-stenting pressure drop model. According to an advantageous implementation, the post-stenting FFR values for each of the stenting strategies can be computed under the assumption that each stenting will be fully successful by using a fully successful modified post-stenting pressure drop model to predict the post-stenting pressure drop for each stented stenosis region. This allows the treatment planning method to virtually eliminate the functional role of individual stenosis regions or multiple stenosis regions without having to modify the geometry of the vessel in the presence of a stent. This could be used to reduce the possible stenting strategies, and in a possible embodiment, step 610 can be repeated for the remaining stenting strategies that were not eliminated using the partially successful modified post-stenting pressure-drop models.

At step 612, the predicted post-stenting FFR computation results for the plurality of stenting strategies are output. For example, the predicted post-stenting FFR computation results for each of stenting strategies can be displayed on a display device, either by listing the predicted post-stenting FFR values or overlaying the predicted post-stenting FFR on medical image data of the patient.

Figure 8:
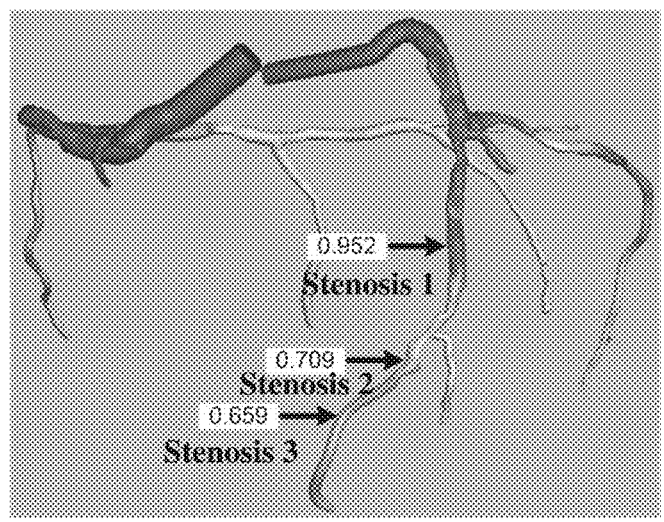
FIGS. 8-14 illustrate predicted post-stenting FFR values for different stenting strategies for performing virtual PCI on the coronary artery stenoses of FIG. 7.
Figure 9:
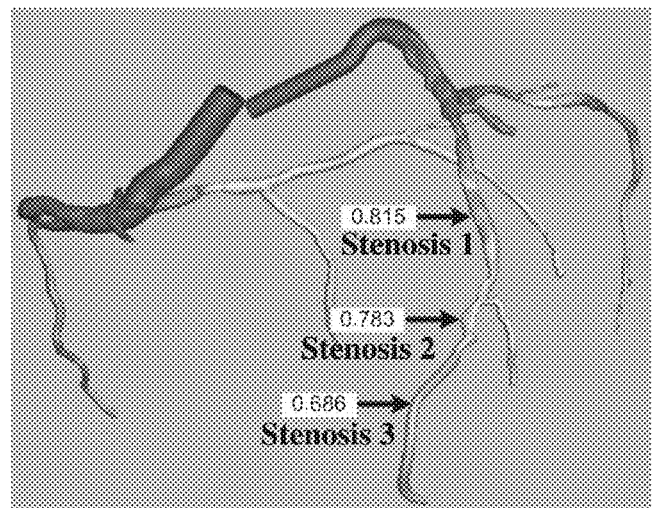
Figure 10:
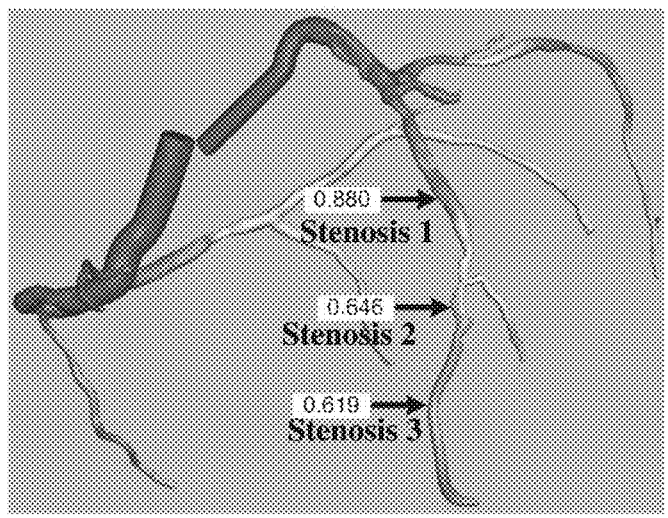
Figure 11:
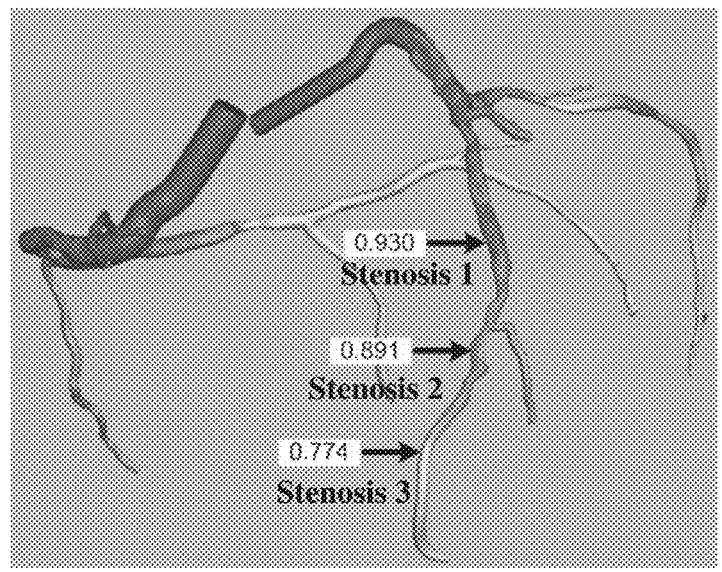
Figure 12:
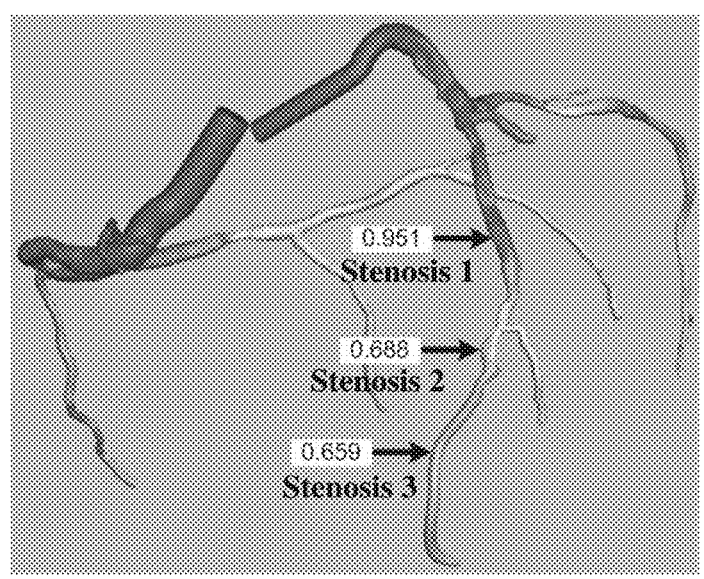
Figure 13:
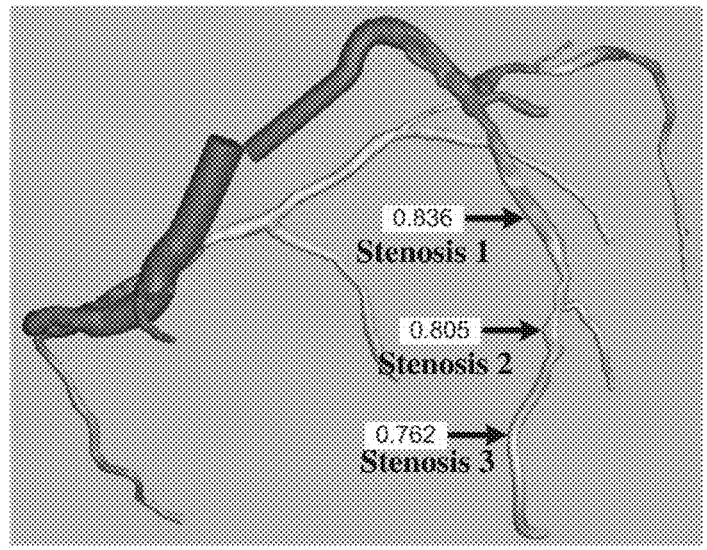
Figure 14:
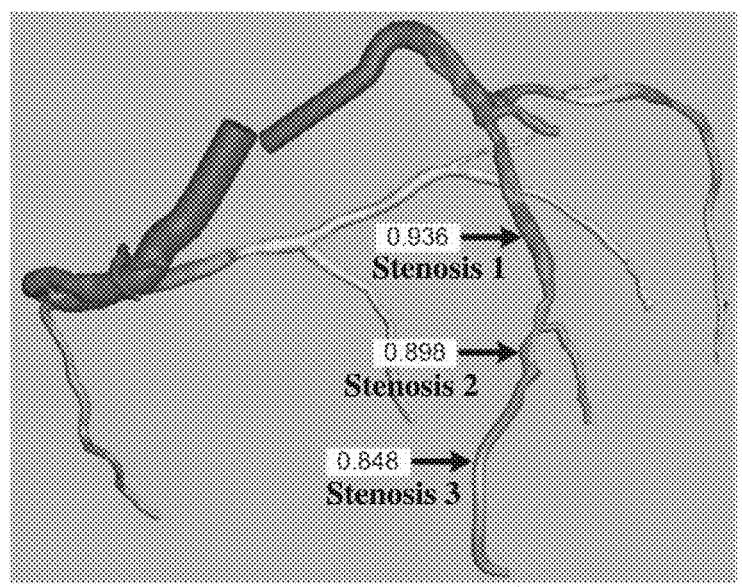

FIGS. 8-14 illustrate predicted post-stenting FFR values for different stenting strategies for performing virtual PCI on the coronary artery stenoses of FIG. 7. FIG. 8 illustrates predicted post-stenting FFR values resulting from virtual PCI (stenting) for stenosis 1. FIG. 9 illustrates predicted post-stenting FFR values resulting from virtual PCI for stenosis 2. FIG. 10 illustrates predicted post-stenting FFR values resulting from virtual PCI for stenosis 3. FIG. 11 illustrates predicted post-stenting FFR values resulting from virtual PCI for stenoses 1 and 2. FIG. 12 illustrates predicted post-stenting FFR values resulting from virtual PCI for stenoses 1 and 3. FIG. 13 illustrates predicted post-stenting FFR values resulting from virtual PCI for stenoses 2 and 3. FIG. 14 illustrates predicted post-stenting FFR values resulting from virtual PCI for stenoses 1, 2, and 3. The results of the virtual post-PCI FFR computations indicate that stenting of all three stenoses is required in order to obtain a distal FFR value higher than 0.8. An important reason for this is due to the fact that when one stenosis is removed, the pressure drop along the remaining stenoses increases due to the increased flow rate, thus leading to a larger drop in the predicted post-stenting FFR value than in the originally computed pre-stenting FFR value.

Figure 15:
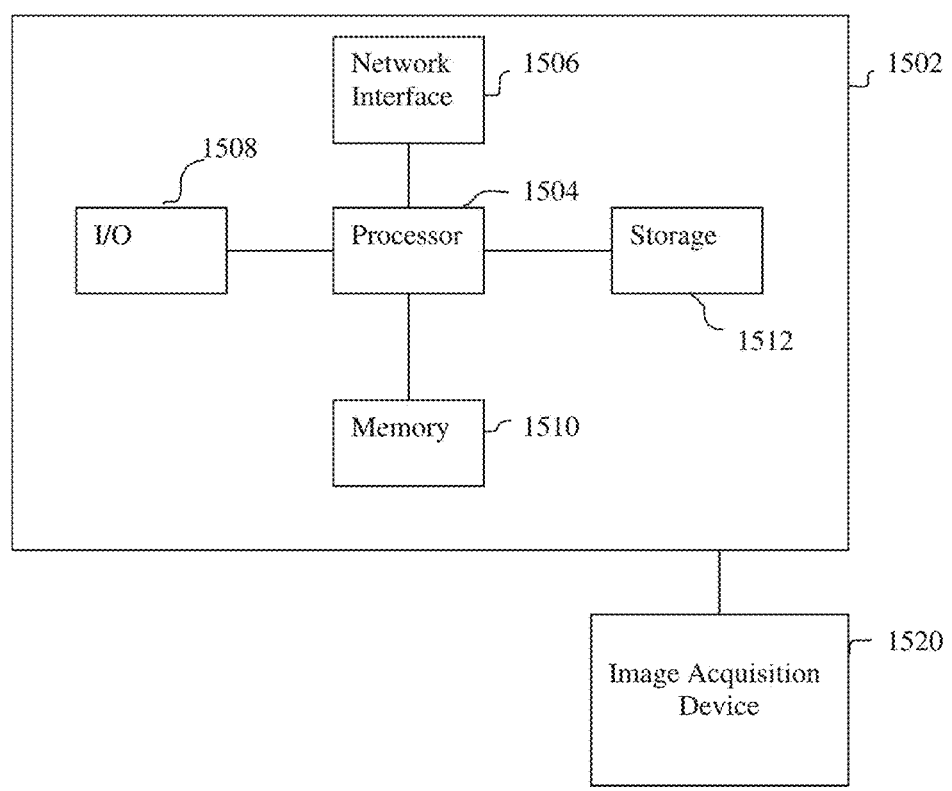
FIG. 15 is a high-level block diagram of a computer capable of implementing the present invention.

The above-described methods for predicting post-stenting hemodynamic metrics of arterial stenosis for treatment planning may be implemented on a computer using well-known computer processors, memory units, storage devices, computer software, and other components. A high-level block diagram of such a computer is illustrated in FIG. 15. Computer 1502 contains a processor 1504, which controls the overall operation of the computer 1502 by executing computer program instructions which define such operation. The computer program instructions may be stored in a storage device 1512 (e.g., magnetic disk) and loaded into memory 1510 when execution of the computer program instructions is desired. Thus, the steps of the methods of FIGS. 1, 5, and 6 may be defined by the computer program instructions stored in the memory 1510 and/or storage 1512 and controlled by the processor 1504 executing the computer program instructions. An image acquisition device 1520, such as a CT scanning device, MR scanning device, Ultrasound device, etc., can be connected to the computer 1502 to input image data to the computer 1502. It is possible to implement the image acquisition device 1520 and the computer 1502 as one device. It is also possible that the image acquisition device 1520 and the computer 1502 communicate wirelessly through a network. In a possible embodiment, the computer 1502 may be located remotely with respect to the image acquisition device 1520 and the method steps are performed as part of a server or cloud based service. The computer 1502 also includes one or more network interfaces 1506 for communicating with other devices via a network. The computer 1502 also includes other input/output devices 1508 that enable user interaction with the computer 1502 (e.g., display, keyboard, mouse, speakers, buttons, etc.). Such input/output devices 1508 may be used in conjunction with a set of computer programs as an annotation tool to annotate volumes received from the image acquisition device 1520. One skilled in the art will recognize that an implementation of an actual computer could contain other components as well, and that FIG. 15 is a high level representation of some of the components of such a computer for illustrative purposes.

The above-described methods for medical image synthesis may be implemented using computers operating in a client-server relationship. Typically, in such a system, the client computers are located remotely from the server computer and interact via a network. The client-server relationship may be defined and controlled by computer programs running on the respective client and server computers.

The above-described methods for medical image synthesis may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 1, 5, and 6. Certain steps of the methods described herein, including one or more of the steps of FIGS. 1, 5, and 6, may be performed by a server or by another processor in a network-based cloud-computing system. Certain steps of the methods described herein, including one or more of the steps of FIGS. 1, 5, and 6, may be performed by a client computer in a network-based cloud computing system. The steps of the methods described herein, including one or more of the steps of FIGS. 1, 5, and 6, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for predicting a post-stenting hemodynamic metric for a coronary artery stenosis from pre-stenting medical image data, comprising:

extracting a pre-stenting patient-specific anatomical model of the coronary arteries from medical image data of a patient;

directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region;

simulating blood flow in the pre-stenting patient-specific anatomical model of the coronary arteries with the modified pressure-drop model used for computing the pressure-drop over the target stenosis region in the pre-stenting patient-specific anatomical model of the coronary arteries, wherein the modified pressure-drop model simulates the effect of stenting on the target stenosis region; and calculating a predicted post-stenting hemodynamic metric for the target stenosis region based on the pressure-drop over the target stenosis region computed using the modified pressure-drop model.

2. The method of claim 1, wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises:

simulating blood flow in the pre-stenting patient-specific anatomical model of the coronary arteries using a computational model of coronary circulation that represents stenosis regions in the pre-stenting patient-specific anatomical model of the coronary arteries with pressure-drop models, wherein the modified pressure-drop model that simulates the effect of stenting on the target stenosis region is used as the pressure-drop representing the target stenosis region to compute the pressure-drop over the target stenosis region in the pre-stenting patient-specific anatomical model of the coronary arteries.

3. The method of claim 1, wherein the modified pressure-drop model is one of a fully successful post-stenting pressure-drop model that simulates the effect of a fully successful stenting treatment on the target stenosis region or a partially successful post-stenting pressure drop model that simulates the effect of a partially successful stenting procedure on the target stenosis region.

4. The method of claim 3, wherein the modified pressure-drop model is the fully successful post-stenting pressure-drop model, and simulating blood flow in the pre-stenting patient-specific anatomical model of the coronary arteries with a modified pressure-drop model for computing a pressure drop over a target stenosis region in the pre-stenting patient-specific anatomical model of the coronary arteries comprises:
  determining an assumed value for a parameter of the modified pressure-drop model to simulate complete enlargement of the target stenosis region without modifying the pre-stenting patient-specific anatomical model of the coronary arteries; and
  computing a predicted post-stenting pressure drop over the target stenosis region based on the simulated blood flow in the pre-stenting patient-specific anatomical model of the coronary arteries using the modified pressure-drop model with the assumed value for the parameter.

5. The method of claim 4, wherein determining an assumed value for a parameter of the modified pressure-drop model to simulate complete enlargement of the target stenosis region without modifying the pre-stenting patient-specific anatomical model of the coronary arteries comprises:
  determining an assumed value for a post-stenting cross-sectional area of a distal portion of the target stenosis region without modifying the pre-stenting patient-specific anatomical model of the coronary arteries.

6. The method of claim 5, wherein the modified pressure-drop model is a fully analytical pressure drop model, and computing a predicted post-stenting pressure drop over the target stenosis region based on the simulated blood flow in the pre-stenting patient-specific anatomical model of the coronary arteries using the modified pressure-drop model with the assumed value for the parameter comprises:
  computing a convection pressure-drop term based on the assumed value for the post-stenting cross-sectional area of the distal portion of the target stenosis region, and computing a viscous pressure drop term based on an average of the assumed value for the post-stenting cross-sectional area of the distal portion of the target stenosis region and a cross-sectional area of a proximal portion of the target stenosis region in the pre-stenting patient-specific anatomical model of the coronary arteries.

7. The method of claim 5, wherein the modified pressure-drop model is a fully analytical pressure drop model, and computing a predicted post-stenting pressure drop over the target stenosis region based on the simulated blood flow in the pre-stenting patient-specific anatomical model of the coronary arteries using the modified pressure-drop model with the assumed value for the parameter comprises:
  computing a convection pressure-drop term based on the assumed value for the post-stenting cross-sectional area of the distal portion of the target stenosis region, and computing a viscous pressure drop term based on an interpolation between a cross-sectional area of a proximal portion of the target stenosis region in the pre-stenting patient-specific anatomical model of the coronary arteries and the assumed value for the post-stenting cross-sectional area of the distal portion of the target stenosis region.

8. The method of claim 5, wherein the modified pressure-drop model is a semi-empirical pressure drop model and computing a predicted post-stenting pressure drop over the target stenosis region based on the simulated blood flow in the pre-stenting patient-specific anatomical model of the coronary arteries using the modified pressure-drop model with the assumed value for the parameter comprises:
  computing a convection pressure-drop term based on the assumed value for the post-stenting cross-sectional area of the distal portion of the target stenosis region, and computing a viscous pressure drop term based on a viscous coefficient that is adapted to correspond to the assumed value for the post-stenting cross-sectional area of the distal portion of the target stenosis region.

9. The method of claim 3, wherein the modified pressure-drop model is the partially successful post-stenting pressure drop model;
  wherein directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region, comprises: determining assumed values for one or more parameters of the modified pressure-drop model to simulate partial enlargement of the target stenosis region without modifying the pre-stenting patient-specific anatomical model of the coronary arteries; and
  wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises: computing a predicted post-stenting pressure-drop over the target stenosis region based on the simulated blood flow in the pre-stenting patient-specific anatomical model of the coronary arteries using the modified pressure-drop model with the assumed values for the one or more parameters.

10. The method of claim 9, wherein determining assumed values for one or more parameters of the modified pressure-drop model to simulate partial enlargement of the target stenosis region without modifying the pre-stenting patient-specific anatomical model of the coronary arteries comprises:
  determining an assumed value for each of a post-stenting cross-sectional area of a distal portion of the target stenosis region and a post-stenting minimum cross-sectional area of the target stenosis region without modifying the pre-stenting patient-specific anatomical model of the coronary arteries.

11. The method of claim 10, wherein the modified pressure-drop model is a fully analytical pressure drop model, and computing a predicted post-stenting pressure-drop over the target stenosis region based on the simulated blood flow in the pre-stenting patient-specific anatomical model of the coronary arteries using the modified pressure-drop model with the assumed values for the one or more parameters comprises:

computing a convection pressure-drop term based on the assumed value for the post-stenting cross-sectional area of the distal portion of the target stenosis region, computing a viscous pressure drop term along an entire length of the target stenosis region based on the assumed values for the post-stenting cross-sectional area of the distal portion of the target stenosis region and the post-stenting minimum cross-sectional area of the target stenosis region, and computing an expansion pressure drop term based on the assumed values for the post-stenting cross-sectional area of the distal portion of the target stenosis region and the post-stenting minimum cross-sectional area of the target stenosis region.

12. The method of claim 10, wherein the modified pressure-drop model is a semi-empirical pressure drop model, and computing a predicted post-stenting pressure drop over the target stenosis region based on the simulated blood flow in the pre-stenting patient-specific anatomical model of the coronary arteries using the modified pressure-drop model with the assumed value for the one or more parameters comprises:

computing a convection pressure-drop term based on the assumed value for the post-stenting cross-sectional area of the distal portion of the target stenosis region, computing a viscous pressure drop term based on an adapted viscous coefficient, and computing an expansion pressure drop term based on the assumed values for the post-stenting cross-sectional area of the distal portion of the target stenosis region and the post-stenting minimum cross-sectional area of the target stenosis region.

13. The method of claim 3, wherein directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region, comprises:

selecting one of the fully successful post-stenting pressure-drop model or the partially successful post-stenting pressure drop model for the target stenosis region, and determining an assumed value for at least one parameter of the modified pressure-drop model to simulate complete or partial enlargement of the target stenosis region without modifying the pre-stenting patient-specific anatomical model of the coronary arteries based on the selection of one of the fully successful post-stenting pressure-drop model or the partially successful post-stenting pressure drop model for the target stenosis region; and wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises:

computing a predicted post-stenting pressure-drop over the target stenosis region based on the simulated blood flow in the pre-stenting patient-specific anatomical model of the coronary arteries using the modified pressure-drop model with the assumed value for at least one parameter.

14. The method of claim 13, wherein selecting one of the fully successful post-stenting pressure-drop model or the partially successful post-stenting pressure drop model for the target stenosis region comprises:

displaying a prompt requesting a user selection of the fully successful post-stenting pressure-drop model or the partially successful post-stenting pressure drop model; and selecting the one of the fully successful post-stenting pressure-drop model or the partially successful post-stenting pressure drop model for the target stenosis region based on a received user selection.

15. The method of claim 13, wherein selecting one of the fully successful post-stenting pressure-drop model or the partially successful post-stenting pressure drop model for the target stenosis region comprises:

automatically selecting one of the fully successful post-stenting pressure-drop model or the partially successful post-stenting pressure drop model based on image features extracted from a region of interest corresponding to the target stenosis region in the medical image data.

16. The method of claim 15, wherein automatically selecting one of the fully successful post-stenting pressure-drop model or the partially successful post-stenting pressure drop model based on image features extracted from a region of interest corresponding to the target stenosis region in the medical image data comprises:

quantifying an amount of calcification for the target stenosis region based on the features extracted from the region of interest corresponding to the target stenosis region in the medical image data; and automatically selecting one of the fully successful post-stenting pressure-drop model or the partially successful post-stenting pressure drop model based on the quantified amount of calcification for the target stenosis region.

17. The method of claim 1, wherein calculating a predicted post-stenting hemodynamic metric for the target stenosis region based on the pressure-drop over the target stenosis region computed using the modified pressure-drop model comprises:

calculating a predicted post-stenting fractional flow reserve (FFR) value for the target stenosis region based on the pressure-drop over the target stenosis region computed using the modified pressure-drop model.

18. The method of claim 1, further comprising:

repeating the steps of directly modifying one or more parameters of a pressure-drop model that computes a pressure-drop over a target stenosis region in the pre-stenting anatomical model of the coronary arteries without modifying the pre-stenting patient-specific anatomical model of the coronary arteries, simulating blood flow in the pre-stenting patient-specific anatomical model of the coronary arteries with the modified pressure-drop model used for computing the pressure-drop over the target stenosis region in the pre-stenting patient-specific anatomical model of the coronary arteries, and calculating a predicted post-stenting hemodynamic metric for the target stenosis region based on the pressure-drop over the target stenosis region computed using the modified pressure-drop model, for each of a plurality of target stenosis regions individually and for all possible combinations of the plurality of target stenosis regions to predict post-stenting hemodynamic metrics corresponding to multiple possible stenting scenarios.

19. A method for automated virtual planning of a stenting treatment to treat coronary artery stenoses of a patient, comprising:

extracting a pre-stenting patient-specific anatomical model of the coronary arteries from medical image data of a patient;

computing pre-stenting fractional flow reserve (FFR) values for a plurality of stenosis regions in the pre-stenting patient-specific anatomical model of the coronary arteries based on simulated blood flow and pressure in the pre-stenting patient-specific anatomical model of the coronary arteries;

determining a plurality of virtual stenting strategies based on the pre-stenting FFR values computed for the plurality of stenosis regions;

predicting post-stenting FFR values for the plurality of stenosis regions resulting from each of the plurality of virtual stenting strategies, wherein each virtual stenting strategy designates one or more of the stenosis regions to be stented and, for each virtual stenting strategy, the predicted post-stenting FFR values for the plurality of stenosis regions are computed by:

directly modifying one or more parameters of a respective pressure-drop model that computes a pressure-drop over each of the one or more stenosis regions in the pre-stenting anatomical model of the coronary arteries without modifying the pre-stenting patient-specific anatomical model of the coronary arteries, resulting in a respective modified pressure-drop model for each of the one or more stenosis regions that simulates an effect of stenting on that stenosis region, and simulating blood flow in the pre-stenting patient-specific anatomical model of the coronary arteries with the respective modified pressure-drop model used to compute a post-stenting pressure-drop for each of the one or more of the stenosis regions designated to be stented in that stenting strategy.

20. The method of claim 19, wherein determining a plurality of virtual stenting strategies based on the pre-stenting FFR values computed for the plurality of stenosis regions comprises:

identifying a stenosis region having an FFR value less than a predetermined threshold and one or more preceding stenosis regions in the pre-stenting patient-specific anatomical model of the coronary arteries to be included in a set of target stenosis regions; and determining the plurality of virtual stenting strategies to include respective virtual stenting strategies that designate each of the target stenosis regions to be stented individually and each possible combination of multiple ones of the target stenosis regions to be stented.

21. The method of claim 20, wherein predicting post-stenting FFR values for the plurality of stenosis regions resulting from each of the plurality of virtual stenting strategies comprises:

predicting the post-stenting FFR values for the plurality of stenosis regions resulting from each of the plurality of virtual stenting strategies using a fully successful post-stenting pressure-drop model that simulates a fully successful stenting treatment as the modified pressure-drop model used to compute the post-stenting pressure drop for each of the one or more target stenosis regions designated to be stented in each of the plurality of stenting strategies.

22. The method of claim 20, further comprising:

identifying at least one of the plurality of virtual stenting strategies that results in predicted posting-stenting FFR values less than the predetermined threshold for each of the plurality of stenosis regions.

23. An apparatus for predicting a post-stenting hemodynamic metric for a coronary artery stenosis from pre-stenting medical image data, comprising:

a processor; and a memory storing computer program instructions, which when executed by the processor cause the processor to perform operations comprising:

extracting a pre-stenting patient-specific anatomical model of the coronary arteries from medical image data of a patient;

directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region;

simulating blood flow in the pre-stenting patient-specific anatomical model of the coronary arteries with the modified pressure-drop model used for computing a pressure-drop over the target stenosis region in the pre-stenting patient-specific anatomical model of the coronary arteries, wherein the modified pressure-drop model simulates the effect of stenting on the target stenosis region; and calculating a predicted post-stenting hemodynamic metric for the target stenosis region based on the pressure-drop over the target stenosis region computed using the modified pressure-drop model.

24. The apparatus of claim 23, wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises:

simulating blood flow in the pre-stenting patient-specific anatomical model of the coronary arteries using a computational model of coronary circulation that represents stenosis regions in the pre-stenting patient-specific anatomical model of the coronary arteries with pressure-drop models, wherein the modified pressure-drop model that simulates the effect of stenting on the target stenosis region is used as the pressure-drop representing the target stenosis region to compute the pressure-drop over the target stenosis region in the pre-stenting patient-specific anatomical model of the coronary arteries.

25. The apparatus of claim 23, wherein the modified pressure-drop model is one of a fully successful post-stenting pressure-drop model that simulates the effect of a fully successful stenting treatment on the target stenosis region or a partially successful post-stenting pressure drop model that simulates the effect of a partially successful stenting procedure on the target stenosis region.

26. The apparatus of claim 25, wherein the modified pressure-drop model is the fully successful post-stenting pressure-drop model, and the simulating blood flow in the pre-stenting patient-specific anatomical model of the coronary arteries with a modified pressure-drop model for computing a pressure drop over a target stenosis region in the pre-stenting patient-specific anatomical model of the coronary arteries comprises:

determining an assumed value for a parameter of the modified pressure-drop model to simulate complete enlargement of the target stenosis region without modifying the pre-stenting patient-specific anatomical model of the coronary arteries; and computing a predicted post-stenting pressure drop over the target stenosis region based on the simulated blood flow in the pre-stenting patient-specific anatomical model of the coronary arteries using the modified pressure-drop model with the assumed value for the parameter.

27. The apparatus of claim 26, wherein the determining an assumed value for a parameter of the modified pressure-drop model to simulate complete enlargement of the target stenosis region without modifying the pre-stenting patient-specific anatomical model of the coronary arteries comprises:

determining an assumed value for a post-stenting cross-sectional area of a distal portion of the target stenosis region without modifying the pre-stenting patient-specific anatomical model of the coronary arteries.

28. The apparatus of claim 25, wherein the modified pressure-drop model is the partially successful post-stenting pressure drop model;

wherein directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region, comprises: determining assumed values for one or more parameters of the modified pressure-drop model to simulate partial enlargement of the target stenosis region without modifying the pre-stenting patient-specific anatomical model of the coronary arteries; and wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises: computing a predicted post-stenting pressure-drop over the target stenosis region based on the simulated blood flow in the pre-stenting patient-specific anatomical model of the coronary arteries using the modified pressure-drop model with the assumed values for the one or more parameters.

29. The apparatus of claim 28, wherein determining assumed values for one or more parameters of the modified pressure-drop model to simulate partial enlargement of the target stenosis region without modifying the pre-stenting patient-specific anatomical model of the coronary arteries comprises:

determining an assumed value for each of a post-stenting cross-sectional area of a distal portion of the target stenosis region and a post-stenting minimum cross-sectional area of the target stenosis region without modifying the pre-stenting patient-specific anatomical model of the coronary arteries.

30. The apparatus of claim 25, wherein directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region, comprises:

selecting one of the fully successful post-stenting pressure-drop model or the partially successful post-stenting pressure drop model for the target stenosis region, and determining an assumed value for at least one parameter of the modified pressure-drop model to simulate complete or partial enlargement of the target stenosis region without modifying the pre-stenting patient-specific anatomical model of the coronary arteries based on the selection of one of the fully successful post-stenting pressure-drop model or the partially successful post-stenting pressure drop model for the target stenosis region; and wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises:

computing a predicted post-stenting pressure-drop over the target stenosis region based on the simulated blood flow in the pre-stenting patient-specific anatomical model of the coronary arteries using the modified pressure-drop model with the assumed value for at least one parameter.

31. The apparatus of claim 30, wherein selecting one of the fully successful post-stenting pressure-drop model or the partially successful post-stenting pressure drop model for the target stenosis region comprises:

automatically selecting one of the fully successful post-stenting pressure-drop model or the partially successful post-stenting pressure drop model based on image features extracted from a region of interest corresponding to the target stenosis region in the medical image data.

32. The apparatus of claim 23, wherein calculating a predicted post-stenting hemodynamic metric for the target stenosis region based on the pressure-drop over the target stenosis region computed using the modified pressure-drop model comprises:

calculating a predicted post-stenting fractional flow reserve (FFR) value for the target stenosis region based on the pressure-drop over the target stenosis region computed using the modified pressure-drop model.

33. An apparatus for automated virtual planning of a stenting treatment to treat coronary artery stenoses of a patient, comprising:

a processor; and a memory storing computer program instructions, which when executed by the processor causes the processor to perform operations comprising:

extracting a pre-stenting patient-specific anatomical model of the coronary arteries from medical image data of a patient;

computing pre-stenting fractional flow reserve (FFR) values for a plurality of stenosis regions in the pre-stenting patient-specific anatomical model of the coronary arteries based on simulated blood flow and pressure in the pre-stenting patient-specific anatomical model of the coronary arteries;

determining a plurality of virtual stenting strategies based on the pre-stenting FFR values computed for the plurality of stenosis regions;

predicting post-stenting FFR values for the plurality of stenosis regions resulting from each of the plurality of virtual stenting strategies, wherein each virtual stenting strategy designates one or more of the stenosis regions to be stented and, for each of the plurality of virtual stenting strategies, the predicted post-stenting FFR values for the plurality of stenosis regions are computed by:
  directly modifying one or more parameters of a respective pressure-drop model that computes a pressure-drop over each of the one or more stenosis regions in the pre-stenting anatomical model of the coronary arteries without modifying the pre-stenting patient-specific anatomical model of the coronary arteries, resulting in a respective modified pressure-drop model for each of the one or more stenosis regions that simulates an effect of stenting on that stenosis region, and
  simulating blood flow in the pre-stenting patient-specific anatomical model of the coronary arteries with the respective modified pressure-drop model used to compute a post-stenting pressure-drop for each of the one or more of the stenosis regions designated to be stented in that stenting strategy.

34. A non-transitory computer readable medium storing computer program instructions for predicting a post-stenting hemodynamic metric for a coronary artery stenosis from pre-stenting medical image data, the computer program instructions when executed by a processor cause the processor to perform operations comprising:
  extracting a pre-stenting patient-specific anatomical model of the coronary arteries from medical image data of a patient;
  directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region;
  simulating blood flow in the pre-stenting patient-specific anatomical model of the coronary arteries with the modified pressure-drop model used for computing the pressure-drop over the target stenosis region in the pre-stenting patient-specific anatomical model of the coronary arteries, wherein the modified pressure-drop model simulates the effect of stenting on the target stenosis region; and
  calculating a predicted post-stenting hemodynamic metric for the target stenosis region based on the pressure-drop over the target stenosis region computed using the modified pressure-drop model.

35. The non-transitory computer readable medium of claim 34, wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises:
  simulating blood flow in the pre-stenting patient-specific anatomical model of the coronary arteries using a computational model of coronary circulation that represents stenosis regions in the pre-stenting patient-specific anatomical model of the coronary arteries with pressure-drop models, wherein the modified pressure-drop model that simulates the effect of stenting on the target stenosis region is used as the pressure-drop representing the target stenosis region to compute the pressure-drop over the target stenosis region in the pre-stenting patient-specific anatomical model of the coronary arteries.

36. The non-transitory computer readable medium of claim 34, wherein the modified pressure-drop model is one of a fully successful post-stenting pressure-drop model that simulates the effect of a fully successful stenting treatment on the target stenosis region or a partially successful post-stenting pressure drop model that simulates the effect of a partially successful stenting procedure on the target stenosis region.

37. The non-transitory computer readable medium of claim 36, wherein the modified pressure-drop model is the fully successful post-stenting pressure-drop model, and simulating blood flow in the pre-stenting patient-specific anatomical model of the coronary arteries with a modified pressure-drop model for computing a pressure drop over a target stenosis region in the pre-stenting patient-specific anatomical model of the coronary arteries comprises:
  determining an assumed value for a parameter of the modified pressure-drop model to simulate complete enlargement of the target stenosis region without modifying the pre-stenting patient-specific anatomical model of the coronary arteries; and
  computing a predicted post-stenting pressure drop over the target stenosis region based on the simulated blood flow in the pre-stenting patient-specific anatomical model of the coronary arteries using the modified pressure-drop model with the assumed value for the parameter.

38. The non-transitory computer readable medium of claim 37, wherein determining an assumed value for a parameter of the modified pressure-drop model to simulate complete enlargement of the target stenosis region without modifying the pre-stenting patient-specific anatomical model of the coronary arteries comprises:
  determining an assumed value for a post-stenting cross-sectional area of a distal portion of the target stenosis region without modifying the pre-stenting patient-specific anatomical model of the coronary arteries.

39. The non-transitory computer readable medium of claim 36, wherein the modified pressure-drop model is the partially successful post-stenting pressure drop model;
  wherein directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region, comprises: determining assumed values for one or more parameters of the modified pressure-drop model to simulate partial enlargement of the target stenosis region without modifying the pre-stenting patient-specific anatomical model of the coronary arteries; and
  wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises: computing a predicted post-stenting pressure-drop over the target stenosis region based on the simulated blood flow in the pre-stenting patient-specific anatomical model of the coronary arteries using the modified pressure-drop model with the assumed values for the one or more parameters.

40. The non-transitory computer readable medium of claim 39, wherein determining assumed values for one or more parameters of the modified pressure-drop model to simulate partial enlargement of the target stenosis region without modifying the pre-stenting patient-specific anatomical model of the coronary arteries comprises:
   determining an assumed value for each of a post-stenting cross-sectional area of a distal portion of the target stenosis region and a post-stenting minimum cross-sectional area of the target stenosis region without modifying the pre-stenting patient-specific anatomical model of the coronary arteries.

41. The non-transitory computer readable medium of claim 36, wherein directly modifying one or more parameters of a pressure-drop model that computes a pressure-drop over a target stenosis region in the pre-stenting anatomical model of the coronary arteries without modifying the pre-stenting patient-specific anatomical model of the coronary arteries, resulting in a modified pressure-drop model that simulates an effect of stenting on the target stenosis region, comprises:
   selecting one of the fully successful post-stenting pressure-drop model or the partially successful post-stenting pressure drop model for the target stenosis region, and
   determining an assumed value for at least one parameter of the modified pressure-drop model to simulate complete or partial enlargement of the target stenosis region without modifying the pre-stenting patient-specific anatomical model of the coronary arteries based on the selection of one of the fully successful post-stenting pressure-drop model or the partially successful post-stenting pressure drop model for the target stenosis region; and
   wherein simulating blood flow in the pre-stenting patient-specific anatomical model of the coronary arteries with the modified pressure-drop model used for computing the pressure-drop over the target stenosis region in the pre-stenting patient-specific anatomical model of the coronary arteries comprises:
   computing a predicted post-stenting pressure-drop over the target stenosis region based on the simulated blood flow in the pre-stenting patient-specific anatomical model of the coronary arteries using the modified pressure-drop model with the assumed value for at least one parameter.

42. The non-transitory computer readable medium of claim 41, wherein selecting one of the fully successful post-stenting pressure-drop model or the partially successful post-stenting pressure drop model for the target stenosis region comprises:
   displaying a prompt requesting a user selection of the fully successful post-stenting pressure-drop model or the partially successful post-stenting pressure drop model; and
   selecting the one of the fully successful post-stenting pressure-drop model or the partially successful post-stenting pressure drop model for the target stenosis region based on a received user selection.

43. The non-transitory computer readable medium of claim 41, wherein selecting one of the fully successful post-stenting pressure-drop model or the partially successful post-stenting pressure drop model for the target stenosis region comprises:
   automatically selecting one of the fully successful post-stenting pressure-drop model or the partially successful post-stenting pressure drop model based on image features extracted from a region of interest corresponding to the target stenosis region in the medical image data.

44. The non-transitory computer readable medium of claim 43, wherein automatically selecting one of the fully successful post-stenting pressure-drop model or the partially successful post-stenting pressure drop model based on image features extracted from a region of interest corresponding to the target stenosis region in the medical image data comprises:
   quantifying an amount of calcification for the target stenosis region based on the features extracted from the region of interest corresponding to the target stenosis region in the medical image data; and
   automatically selecting one of the fully successful post-stenting pressure-drop model or the partially successful post-stenting pressure drop model based on the quantified amount of calcification for the target stenosis region.

45. The non-transitory computer readable medium of claim 34, wherein calculating a predicted post-stenting hemodynamic metric for the target stenosis region based on the pressure-drop over the target stenosis region computed using the modified pressure-drop model comprises:
   calculating a predicted post-stenting fractional flow reserve (FFR) value for the target stenosis region based on the pressure-drop over the target stenosis region computed using the modified pressure-drop model.

46. The non-transitory computer readable medium of claim 34, wherein the operations further comprise:
   repeating the operations of directly modifying one or more parameters of a pressure-drop model that computes a pressure-drop over a target stenosis region in the pre-stenting anatomical model of the coronary arteries without modifying the pre-stenting patient-specific anatomical model of the coronary arteries, simulating blood flow in the pre-stenting patient-specific anatomical model of the coronary arteries with the modified pressure-drop model used for computing the pressure-drop over the target stenosis region in the pre-stenting patient-specific anatomical model of the coronary arteries, and calculating a predicted post-stenting hemodynamic metric for the target stenosis region based on the pressure-drop over the target stenosis region computed using the modified pressure-drop model, for each of a plurality of target stenosis regions individually and for all possible combinations of the plurality of target stenosis regions to predict post-stenting hemodynamic metrics corresponding to multiple possible stenting scenarios.

47. A non-transitory computer readable medium storing computer program instructions for automated virtual planning of a stenting treatment to treat coronary artery stenoses of a patient, the computer program instructions when executed by a processor cause the processor to perform operations comprising:
   extracting a pre-stenting patient-specific anatomical model of the coronary arteries from medical image data of a patient;
   computing pre-stenting fractional flow reserve (FFR) values for a plurality of stenosis regions in the pre-stenting patient-specific anatomical model of the coronary arteries based on simulated blood flow and pressure in the pre-stenting patient-specific anatomical model of the coronary arteries;

determining a plurality of virtual stenting strategies based on the pre-stenting FFR values computed for the plurality of stenosis regions;

predicting post-stenting FFR values for the plurality of stenosis regions resulting from each of the plurality of virtual stenting strategies, wherein each virtual stenting strategy designates one or more of the stenosis regions to be stented and, for each virtual stenting strategy, the predicted post-stenting FFR values for the plurality of stenosis regions are computed by:

directly modifying one or more parameters of a respective pressure-drop model that computes a pressure-drop over each of the one or more stenosis regions in the pre-stenting anatomical model of the coronary arteries without modifying the pre-stenting patient-specific anatomical model of the coronary arteries, resulting in a respective modified pressure-drop model for each of the one or more stenosis regions that simulates an effect of stenting on that stenosis region, and simulating blood flow in the pre-stenting patient-specific anatomical model of the coronary arteries with the respective modified pressure-drop model used to compute a post-stenting pressure-drop for each of the one or more of the stenosis regions designated to be stented in that stenting strategy.

48. The non-transitory computer readable medium of claim 47, wherein determining a plurality of virtual stenting strategies based on the pre-stenting FFR values computed for the plurality of stenosis regions comprises:

identifying a stenosis region having an FFR value less than a predetermined threshold and one or more preceding stenosis regions in the pre-stenting patient-specific anatomical model of the coronary arteries to be included in a set of target stenosis regions; and determining the plurality of virtual stenting strategies to include respective virtual stenting strategies that designate each of the target stenosis regions to be stented individually and each possible combination of multiple ones of the target stenosis regions to be stented.

49. The non-transitory computer readable medium of claim 48, wherein predicting post-stenting FFR values for the plurality of stenosis regions resulting from each of the plurality of virtual stenting strategies comprises:

predicting the post-stenting FFR values for the plurality of stenosis regions resulting from each of the plurality of virtual stenting strategies using a fully successful post-stenting pressure-drop model that simulates a fully successful stenting treatment as the modified pressure-drop model used to compute the post-stenting pressure drop for each of the one or more target stenosis regions designated to be stented in each of the plurality of stenting strategies.

50. The non-transitory computer readable medium of claim 48, wherein the operations further comprise:

identifying at least one of the plurality of virtual stenting strategies that results in predicted posting-stenting FFR values less than the predetermined threshold for each of the plurality of stenosis regions.

\* \* \* \* \*